United States Patent [19]

Steiner et al.

[11] Patent Number: 5,015,780
[45] Date of Patent: May 14, 1991

[54] PROCESS FOR THE PREPARATION OF DIHALOBUTYRALDEHYDES

[75] Inventors: Heinz Steiner, Münchenstein; Hans Tobler, Allschwill, both of Switzerland

[73] Assignee: Ciba-Geigy Corporation, Ardsley, N.Y.

[21] Appl. No.: 465,813

[22] Filed: Jan. 16, 1990

[30] Foreign Application Priority Data

Feb. 2, 1989 [CH] Switzerland .................. 364/89

[51] Int. Cl.$^5$ .................. C07C 45/61; C07C 47/14
[52] U.S. Cl. .................. 568/490; 568/458; 568/462; 568/495
[58] Field of Search .............. 568/458, 462, 495, 490

[56] References Cited

U.S. PATENT DOCUMENTS

| | | | |
|---|---|---|---|
| 3,996,292 | 12/1976 | Decor | 568/490 |
| 4,008,279 | 2/1977 | Blay | 568/462 |
| 4,190,606 | 2/1980 | Blay | 568/462 |
| 4,613,702 | 9/1986 | Leconte | 568/490 |

OTHER PUBLICATIONS

Houben-Weyl, vol. 4/1C, p. 373 (1980).
Helv. Chim. Acta, vol. 27, p. 185 (1958).

*Primary Examiner*—Werren B. Lone
*Attorney, Agent, or Firm*—Stephen V. O'Brien

[57] ABSTRACT

Dihalobutyraldehydes of formula I

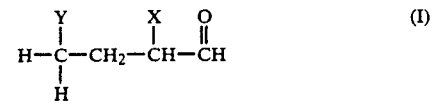

(I)

wherein X and Y are each independently of the other Cl or Br, are obtainable at high rates of conversion and with excellent selectivities by catalytic dehalogenation with hydrogen by carrying out the reaction with appropriate α,α-dihalobutyraldehydes in an organic aprotic solvent. The dihalobutyraldehydes are intermediates for the synthesis of herbicidal acyl cyclohexanediones.

10 Claims, No Drawings

PROCESS FOR THE PREPARATION OF DIHALOBUTYRALDEHYDES

The present invention relates to a process for the preparation of 2,4-chloro- and/or 2,4-bromobutyraldehydes by catalytic dehalogenation with hydrogen in the presence of a hydrogen halide acceptor, which process comprises reacting an appropriate butyraldehyde with a total of two chlorine and/or bromine atoms in 2-position, in an organic aprotic solvent.

The reaction of 2,2-dichloro-ε-caprolactam with hydrogen in the presence of Pd/C and sodium acetate and in glacial acetic acid as solvent to 2-chloro-ε-caprolactam is described in Houben-Weyl, Vol. 4/1C, page 373 (1980). In Helv. Chem. Acta, 21, page 185 (1958), M. Brenner et al describe the same reaction with Raney nickel, triethanolamine and methanol as solvent. The reactions afford the desired 2-chloro-ε-caprolactam in moderate to good yields with moderate selectivities. The catalytic reaction of α,α-dihaloaldehydes with hydrogen has not yet been described in the literature.

It has now been found that α,α-dihalobutyraldehydes can be reacted catalytically with hydrogen and in the presence of a hydrogen halide acceptor, at high rates of conversion and with excellent selectivities, to the corresponding α-monohalobutyraldehydes by using an organic aprotic solvent as solvent.

Specifically, the invention relates to a process for the preparation of dihalobutyraldehydes of formula

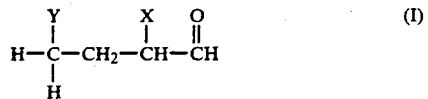

wherein X and Y are each independently of the other Cl or Br, by catalytic dehalogenation of α,α-dihalo compounds with hydrogen, in the presence of a noble metal catalyst or Raney nickel and of a hydrogen halide acceptor and a solvent, in the temperature range from 0°–150° C. and under normal pressure or under a pressure of up to 15 MPa, which process comprises using as α,α-dihalo compound a α,α-dihalobutyraldehyde of formula II

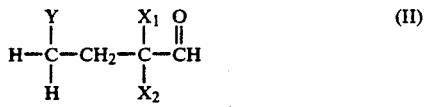

wherein Y has the above meaning and $X_1$ and $X_2$ are each independently of the other Cl or Br, and carrying out the reaction in an organic aprotic solvent.

$X_1$ and $X_2$ in formula II are preferably either Cl or Br. Y is preferably Cl.

In another preferred embodiment of the invention, Y is Cl and X is Cl or Br.

The solvent is preferably selected from the group consisting of hydrocarbons, halogenated hydrocarbons, ethers, ketones, carboxylates, sulfones, N,N-dialkylcarboxamides, N-alkyllactams and lactones.

Illustrative of such solvents are: petroleum ether, pentane, hexen, cyclohexane, methylcyclohexane, benzene, toluene, xylene, chlorobenzene, methylene chloride, chloroform, 1,2-dichloroethane, 1,1,2,2-tetrachloroethane, diethyl ether, dibutyl ether, ethylene glycol dimethyl ether, tetrahydrofuran, dioxane, acetone, methyl isobutyl ketone, methyl or ethyl acetate, tetramethylene sulfone, dimethyl formamide, N-methylpyrrolidone, γ-valerolactone and butyrolactone.

The solvent is preferably polar and aprotic. A particularly preferred solvent is ethyl acetate. The amount of solvent can be chosen within wide limits. It is convenient to use the equivalent to the ten-fold amount of solvent, based on the amount of the compound of formula II.

Hydrogen halide acceptors are commonly known. They may be, typically, tertiary nitrogen bases containing preferably a total of 3 to 20, more particularly 3 to 12, carbon atoms, alkali metal salts of organic acids or of carbonic acid, or oxides or hydroxides of alkali metals or alkaline earth metals. Illustrative of such hydrogen halide acceptors are sodium carbonate, sodium or calcium hydrogen carbonate, sodium acetate, NaOH, KOH, MgO and CaO; or aromatic, aliphatic or cyclic tertiary nitrogen bases such as trimethylamine, triethylamine, tripropylamine, tributylamine, triethanolamine or butyldimethylamine, pyridine, 2,6-dimethylpyridine, N-methylpyrroline and N-methylmorpholine.

Preferred hydrogen halide acceptors are tertiary nitrogen bases and MgO. 2,6-Dimethylpyridine (lutidine) is especially preferred.

A slightly less than equivalent amount or an excess of hydrogen halide acceptor may be used, based on the amount of compound of formula II. It is preferred to use equimolar amounts.

Suitable noble metal catalysts are typically iridium, rhodium, platinum, ruthenium and palladium. Palladium is especially preferred. The noble metal is preferably used on a support. Illustrative of suitable supports are $BaSO_4$, $SiO_2$, $Al_2O_3$ and, in particular, activated carbon. The support may contain 0.1 to 20% by weight of the noble metal. Sulfidated catalysts may also be used. The amount used may be 0.1 to 20% by weight, based on the compound of formula II. It can be expedient to add fresh catalyst in the course of the reaction.

The reaction temperature is preferably in the range from 0° to 80° C., preferably from 0° to 30° C. The pressure is preferably up to 2 MPa. It is preferred to carry out the reaction under normal pressure.

The compounds of formula II are known or obtainable by known methods by α,α-dichlorination or α,α-dibromination of appropriate butyraldehydes. Such methods are described, for example, by P. Martin et al. in Tetrahedron 41, page 4057 (1985), and by H. Rimpler et al. in Chem. Ber. 118, page 4288 (1985).

The compounds of formula I are valuable intermediates for the synthesis of 5-substituted 2-acyl-1,3-cyclohexanediones which may be used as herbicides and for regulating plant growth (q.v. European patent application No. 0 243 313). For this utility, the compound of formula I is converted in manner known per se, for example, to the 1-alkyl- or 1-benzylthio-1-cyclopropane aldehyde and used in the processes disclosed in European patent application No. 0 243 313.

The following examples describe the invention in more detail. The selectivity is determined by gas chromatography.

(A) PREPARATION OF THE STARTING MATERIALS

Example a: Preparation of 2,2-dibromo-4-chlorobutyraldehyde

A mixture of 110 g of 4-chlorobutyraldehyde, 286 g of 5,5-dibromobarbituric acid and 10 ml of HBr in acetic acid (33%) is stirred in 600 ml of ether overnight. The reaction mixture is filtered to remove precipitated solid, and the filtrate is washed twice with water and once with a dilute solution of $NaHCO_3$, dried over $Na_2SO_4$, concentrated by evaporation, and distilled under a high vacuum to afford 81 g of product. Boiling point: 42°–43° C./$3 \times 10^{-2}$ mbar; yield: 90% (determined by gas chromatography).

(B) PREPARATORY EXAMPLES

Example 1

A solution of 351 g of 2,2,4-trichlorobutyraldehyde in 3 l of ethyl acetate is hydrogenated in the presence of 214 g of 2,6-dimethylpyridine and of 18 g of 5% Pd/C catalyst, under normal pressure and at 5°–22° C., until the hydrogen absorption comes to a stop after 7.5 hours. Conversion: 94.3%. Selectivity: 99.9%. After separation of the insoluble constituents, the ethyl acetate is removed by distillation. Vacuum distillation of the residue gives pure 2,4-dichlorobutyraldehyde in 84.5% yield; b.p. 90° C. (68 mbar).

Example 2

A solution of 5.0 g of 2,2,4-trichlorobutyraldehyde in 50 ml of ethyl acetate is hydrogenated in the presence of 3.05 g of 2,6-dimethylpyridine (2,6-lutidine) and of 0.25 g of 5% Pd/C catalyst under normal pressure and at 15°–20° C. The hydrogen absorption comes to a stop after 19 hours. Conversion: 94.3%; selectivity: 99.9%.

Example 3

Hydrogenation is carried out as in Example 2 using 2.88 g of triethylamine in place of 2,6-lutidine. The hydrogenation time is 19 hours. Conversion: 86%; selectivity: 99.7%.

Example 4

The procedure of Example 2 is repeated, using 1.15 g of MgO in place of 2,6-lutidine. The hydrogenation time is almost 7 hours and has to be stopped. Conversion: 99.91%; selectivity: 96.5%.

Example 5

The procedure of Example 2 is repeated, using 2.34 g of sodium acetate in place of 2,6-lutidine. The hydrogenation time is 25 hours and the hydrogenation has to be stopped. Conversion: 65.7%; selectivity: 85.4%.

Example 6

Hydrogenation is carried out as described in Example 2, but using tetrahydrofuran in place of ethyl acetate. The hydrogenation time is 18 hours. Fresh catalyst is added during the hydrogenation, which has to be stopped when the theoretical quantity of hydrogen is absorbed. Conversion: 96.05%; selectivity: 96.6%.

Example 7

Hydrogenation is carried out as described in Example 2, but using dioxane in place of ethyl acetate. The hydrogenation time is 15 hours. Fresh catalyst is added during the hydrogenation, which has to be stopped when the theoretical quantity of hydrogen is absorbed. Conversion: 93.8%; selectivity: 96.6%.

Example 8

Hydrogenation is carried out as described in Example 2 but using methyl tert-butyl ether in place of ethyl acetate. The hydrogenation time is 18 hours. Fresh catalyst is added during the hydrogenation, which has to be stopped when the theoretical quantity of hydrogen is absorbed. Conversion: 92.4%; selectivity: 93.7%.

Example 9

A solution of 5.0 g of 2,2,4-trichlorobutyraldehyde in 44 ml of ethyl acetate is hydrogenated in the presence of 4.11 g of triethanolamine and of 0.3 g of Raney nickel (washed free of water with alcohol) under normal pressure and at 20°–22° C. The hydrogenation time is 13 hours. During the hydrogenation fresh catalyst has to be added. Conversion: 89%; selectivity: 94.4%.

Example 10

A solution of 5.0 g of 2,2-dibromo-4-chlorobutyraldehyde in 50 ml of ethyl acetate is hydrogenated in the presence of 1.82 g of 2,6-lutidine and of 0.25 g of Pd/C catalyst under normal pressure and at 20°–22° C. During the hydrogenation fresh catalyst has to be added. The hydrogenation is stopped after 3 hours. Conversion: 100%: selectivity: 88%.

Example 11

76 g of 2,2-dibromo-4-chlorobutyraldehyde are hydrogenated in accordance with Example 10. The hydrogenation is stopped after 2 hours. Insoluble matter is removed and the solvent is stripped off. Subsequent distillation gives 39.5 g of 2-bromo-4-chlorobutyraldehyde (95%); b.p. 78°–81° C./22 mbar, corresponding to a yield of 70.4% of theory).

What is claimed is:

1. A process for the preparation of a dihalobutyraldehyde of formula I

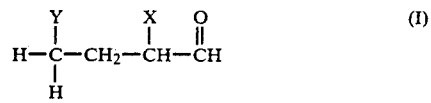

wherein X and Y are each independently of the other Cl or Br, by catalytic dehalogenation of an α,α-dihalo compound with hydrogen in the presence of a noble metal catalyst or Raney nickel and of a hydrogen halide acceptor, in the temperature range from 0°–150° C. and under normal pressure or under a pressure of up to 15 MPa, which process comprises using as α,α-dihalo compound a α,α-dihalobutyraldehyde of formula II

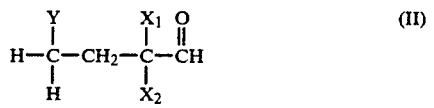

wherein Y has the above meaning and $X_1$ and $X_2$ are each independently of the other Cl or Br, and carrying out the reaction in an organic aprotic solvent.

2. A process according to claim 1, wherein $X_1$ and $X_2$ are either Cl or Br.

3. A process according to claim 1, wherein Y is Cl and X is Cl or Br.

4. A process according to claim 1, wherein the solvent is selected from the group consisting of hydrocarbons, halogenated hydrocarbons, ethers, ketones, carboxylates, sulfones, N,N-dialkylcarboxamides, N-alkyllactams and lactones.

5. A process according to claim 1, wherein the solvent is polar and aprotic.

6. A process according to claim 1, wherein the solvent is ethyl acetate.

7. A process according to claim 1, wherein the hydrogen halide acceptor is a tertiary nitrogen base or magnesium oxide.

8. A process according to claim 7, wherein the nitrogen base is 2,6-dimethylpyridine.

9. A process according to claim 1, wherein the noble metal catalyst is palladium.

10. A process according to claim 1, which is carried out in the temperature range from 0° to 30° C. and under normal pressure.

* * * * *